(12) United States Patent
Gunaratnam et al.

(10) Patent No.: US 7,185,652 B2
(45) Date of Patent: Mar. 6, 2007

(54) GAS DELIVERY CONNECTION ASSEMBLY

(75) Inventors: Michael K. Gunaratnam, Marsfield (AU); Philip R. Kwok, Chatswood (AU); Perry D. Lithgow, Glenwood (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 09/985,457

(22) Filed: Nov. 2, 2001

(65) Prior Publication Data
US 2002/0023649 A1 Feb. 28, 2002

Related U.S. Application Data

(62) Division of application No. 09/498,705, filed on Feb. 7, 2000.

(30) Foreign Application Priority Data

Feb. 9, 1999 (AU) ............................................... PP8550

(51) Int. Cl.
*A61M 16/00* (2006.01)

(52) U.S. Cl. ............................ 128/205.25; 128/204.18; 128/205.24; 128/206.15; 128/202.27

(58) Field of Classification Search ............ 128/204.18, 128/208.21, 204.23, 205.24, 205.25, 206.12, 128/204.29, 204.26, 206.15, 206.21, 207.12; 285/80, 81, 86, 305, 321
See application file for complete search history.

(56) References Cited

U.S. PATENT DOCUMENTS

| 812,706 A | 2/1906 | Warbasse |
|---|---|---|
| 1,653,572 A | 12/1927 | Jackson |
| 2,029,129 A | 1/1936 | Schwartz |

(Continued)

FOREIGN PATENT DOCUMENTS

| CA | 88122 | 11/1999 |
|---|---|---|
| DE | 297 21 766 U1 | 2/1998 |
| DE | 499 00 269.5 | 1/1999 |

(Continued)

OTHER PUBLICATIONS

Japanese Office Action English Translation for JP 2000–029094, 3 pages.
Japanese Office Action English Translation for JP 2000–029094, 3 pages.
ResMed, Mask Systems Product Brochure, 2 pages, Sep. 1992.
Respironics, Inc., "Nasal Mask System Silicone Contour Mask" Product Instructions, 2 pages, Jun. 1997.

*Primary Examiner*—Teena Mitchell
(74) *Attorney, Agent, or Firm*—Nixon & Vanderhye P.C.

(57) ABSTRACT

A patient gas delivery apparatus includes a mask structured to communicate with a patient's airway, a gas flow generator structured to supply pressurized gas, a gas delivery conduit having first and second opposing ends, the first opposing end being connected to the gas flow generator, and a connecting assembly including an anti-asphyxia valve member. The connecting assembly is connected in series between the conduit and the mask. The connecting assembly has a distal end and a proximal end with the distal end being configured and positioned to connect to the second opposing end of the conduit and the proximal end being configured and positioned to connect to the mask. The mask and the conduit are not adapted for direct interconnection without the connecting assembly.

33 Claims, 3 Drawing Sheets

U.S. PATENT DOCUMENTS

| | | | |
|---|---|---|---|
| 2,359,506 A | 10/1944 | Battley et al. | |
| 2,371,965 A | 3/1945 | Lehmberg | |
| 2,823,671 A | 2/1958 | Garelick | |
| 2,893,387 A | 7/1959 | Gongoll et al. | |
| 2,931,356 A * | 4/1960 | Hermann | 128/206.24 |
| 3,189,027 A | 6/1965 | Bartlett, Jr. | |
| 3,474,783 A | 10/1969 | Ulmann | |
| 3,824,999 A | 7/1974 | King | |
| 4,064,875 A * | 12/1977 | Cramer et al. | 128/202.22 |
| 4,111,197 A | 9/1978 | Warncke et al. | |
| 4,121,580 A | 10/1978 | Fabish | |
| 4,164,942 A | 8/1979 | Beard et al. | |
| 4,226,234 A | 10/1980 | Gunderson | |
| 4,274,404 A | 6/1981 | Molzan et al. | |
| 4,494,538 A | 1/1985 | Ansite | |
| 4,506,665 A | 3/1985 | Andrews et al. | |
| 4,580,556 A | 4/1986 | Kondur | |
| 4,606,340 A | 8/1986 | Ansite | |
| 4,622,964 A | 11/1986 | Flynn | |
| 4,794,921 A | 1/1989 | Lindkvist | |
| 4,807,617 A | 2/1989 | Nesti | |
| 4,809,692 A | 3/1989 | Nowacki et al. | |
| 4,841,953 A | 6/1989 | Dodrill | |
| 4,870,963 A | 10/1989 | Carter | |
| 4,875,714 A | 10/1989 | Lee | |
| 4,898,174 A | 2/1990 | Fangrow, Jr. | |
| 4,974,586 A | 12/1990 | Wandel et al. | |
| 4,997,217 A | 3/1991 | Kunze | |
| 5,003,633 A | 4/1991 | Itoh | |
| 5,005,568 A | 4/1991 | Loescher et al. | |
| 5,215,336 A | 6/1993 | Worthing | |
| 5,253,641 A * | 10/1993 | Choate | 128/200.14 |
| 5,311,862 A | 5/1994 | Blasdell et al. | |
| 5,398,973 A | 3/1995 | McAtamney | |
| 5,438,981 A | 8/1995 | Starr et al. | |
| 5,501,214 A | 3/1996 | Sabo | |
| 5,538,001 A | 7/1996 | Bridges | |
| 5,645,049 A | 7/1997 | Foley et al. | |
| 5,647,355 A | 7/1997 | Starr et al. | |
| 5,647,357 A | 7/1997 | Barnett et al. | |
| 5,676,133 A | 10/1997 | Hinckle et al. | |
| 5,709,204 A | 1/1998 | Lester | |
| 5,724,965 A | 3/1998 | Handke et al. | |
| 5,839,436 A | 11/1998 | Fangrow, Jr. et al. | |
| 5,860,677 A | 1/1999 | Martins et al. | |
| 5,878,743 A | 3/1999 | Zdrojkowski et al. | |
| 5,896,857 A | 4/1999 | Hely et al. | |
| 5,909,732 A | 6/1999 | Diesel et al. | |
| 5,921,239 A | 7/1999 | McCall et al. | |
| 5,937,851 A | 8/1999 | Serowski et al. | |
| 5,974,617 A | 11/1999 | Chang | |
| 6,119,693 A | 9/2000 | Kwok et al. | |
| 6,189,532 B1 | 2/2001 | Hely et al. | |
| 6,192,886 B1 | 2/2001 | Rudolph | |
| 6,198,223 B1 | 3/2001 | Scholz | |
| 6,412,487 B1 | 7/2002 | Gunaratnam et al. | |
| 6,491,034 B1 | 12/2002 | Gunaratnam et al. | |
| 6,615,832 B1 | 9/2003 | Chen | |
| 2004/0266948 A1 | 12/2001 | Smith et al. | |
| 2002/0023650 A1 | 2/2002 | Gunaratnam et al. | |
| 2002/0108613 A1 | 8/2002 | Gunaratnam et al. | |

FOREIGN PATENT DOCUMENTS

| | | |
|---|---|---|
| EP | 1 027 905 A3 | 8/2000 |
| ES | 145309 | 1/2000 |
| FR | 2 691 906 | 12/1993 |
| FR | 99/16 | 8/1999 |
| GB | 2080119 | 12/1998 |
| GB | 2080120 | 12/1998 |
| GB | 2080121 | 12/1998 |
| JP | 48-55696 | 7/1973 |
| JP | 59-55535 | 4/1984 |
| JP | 61-67747/86 | 5/1986 |
| JP | 7-21058/95 | 4/1995 |
| JP | 7-308381 | 11/1995 |
| JP | 9-501084 | 2/1997 |
| JP | 1105649 | 2/1999 |
| SE | 65481 | 8/2000 |
| WO | WO 80/01645 | 8/1980 |
| WO | WO 87/01950 | 4/1987 |
| WO | WO 95/04566 | 2/1995 |
| WO | WO 98/26830 | 6/1998 |
| WO | WO 98/48878 | 11/1998 |
| WO | WO 99/30760 | 6/1999 |
| WO | WO 00/38772 | 7/2000 |

\* cited by examiner

GAS DELIVERY CONNECTION ASSEMBLY

This is a Divisional of U.S. application Ser. No. 09/498,705 filed on Feb. 7, 2000 now U.S. Pat. No. 6,491,304, the entirety of which is hereby incorporated herein by reference.

BACKGROUND OF THE INVENTION

This invention relates to improvements in patient gas delivery apparatus of the kind used in the analysis and treatment of respiratory disorders. The invention will be described with particular reference to patient gas delivery apparatus used in the treatment of respiratory disorders such as Obstructive Sleep Apnea (OSA) but it is not intended to be limited thereto.

Patient gas delivery apparatus of the kind having a mask won by a patient and a gas delivery conduit attached to the mask, is commonly used in the analysis and treatment of respiratory disorders. The gas conduit delivers a gas under pressure to the patient. It is necessary that the gas conduit is detachable from the mask to facilitate cleaning.

Patient gas delivery apparatus typically includes at a minimum, a gas delivery conduit and a nose or full face mask. In some cases it is a clinical requirement that additional components be included, such as means for $CO_2$ washout, for example, vents, anti-asphyxia valves and the like. In some cases, these additional components must be assembled un between the gas delivery conduit and the mask. Problems with prior art assemblies include:

(a) They may be inadvertently assembled without the additional components
(b) They may be incorrectly assembled, for example, incorrectly aligned
(c) During the course of treatment, the patient may inadvertently remove or dismantle the assembly and incorrectly reassemble it.

SUMMARY OF THE INVENTION

The present invention is directed towards solving or ameliorating one or more of these problems. The invention will be described with reference to a full face mask and an anti-asphyxia valve, though other forms of mask and additional components may be used.

In one form, the invention resides in a patient gas delivery apparatus including a mask adopted for communication with a patient's airways, a gas flow generator and gas delivery conduit means, further including an assembly connected in series between the conduit means and the mass, said assembly being formed in at least two parts connected by interengaging connecting means, said assembly further including means for connection to the mask, wherein connection of the assembly to the mask prevents disengagement of the interengaging connecting means such that said at least two parts of the assembly cannot separate whilst the assembly is connected to the mask.

In a further form of the invention, there is provided an assembly for connection in series between a gas delivery conduit means and a patient mask in a patient gas delivery apparatus, the assembly being formed in at least two parts connected by interengaging connecting means, said assembly further including means for connection to the mask, wherein connection of the assembly to the mask prevents disengagement of the interengaging connecting means such that said at least two parts of the assembly cannot separate whilst the assembly is connected to the mask.

Preferably, the means for connection to the mask includes locking means located on the inner side of the mask, that is in the region of the mask that lies adjacent the patient's face, such that the assembly cannot be disconnected from the mask until the mask has been substantially removed from the patient.

Preferably also, the interengaging means connecting the two par of the assembly includes detent means on a first of the parts which releasably engage a second of the parts, the detents being held in an engaged position by the mask whilst the assembly is connected to the mask.

Desirably, the mask and conduit are not adapted for direct interconnection without the assembly.

In one preferred form of the invention, the assembly may form a housing for one or more internal components, for example a valve member or a flow sensor.

Further preferred embodiments of the invention will now be described by way of example only with reference to the accompanying drawings in which.

Figure 1:
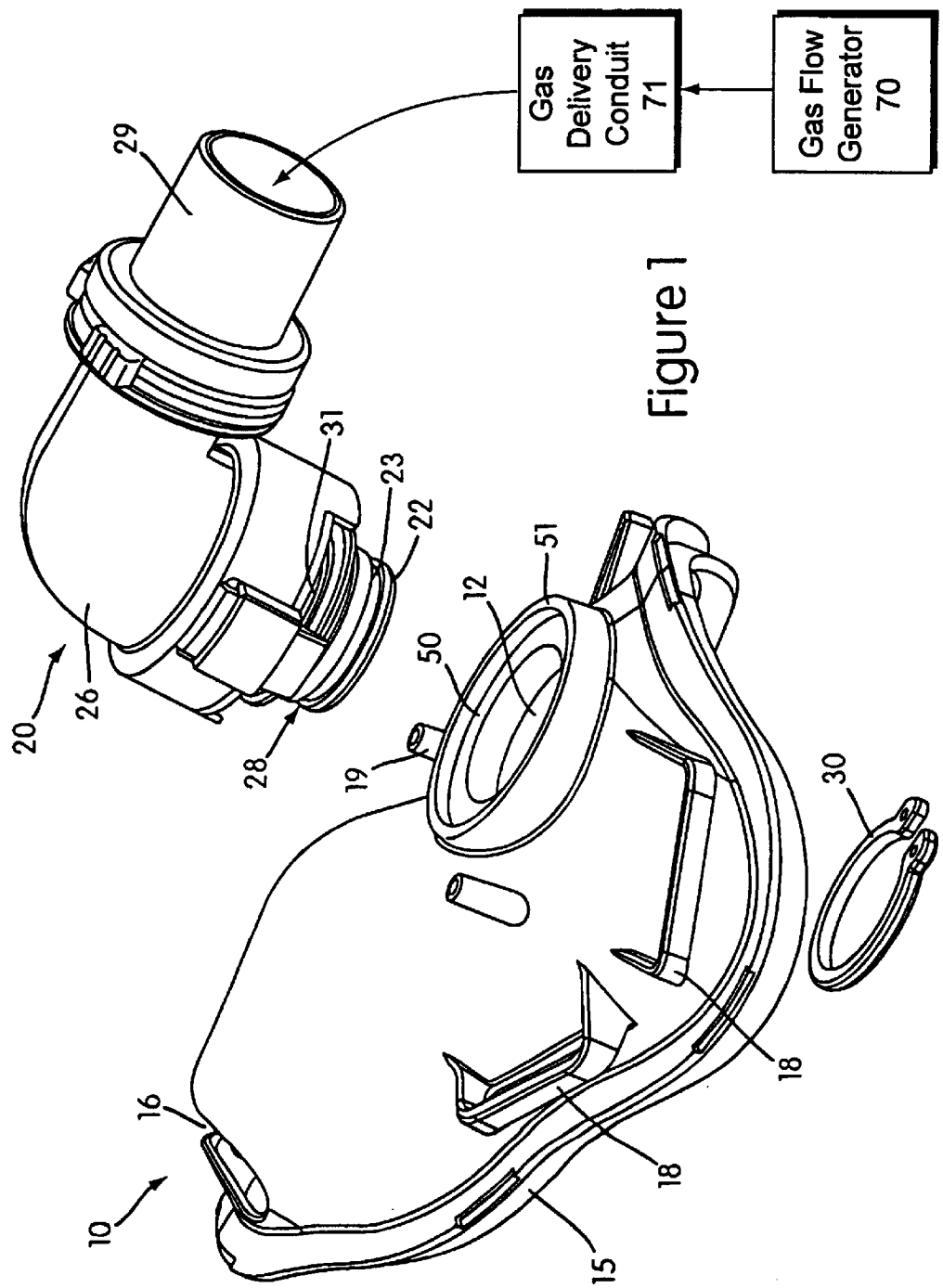
FIG. 1 is a perspective view showing the mask, anti-asphyxia valve housing and conduit connection assembly.

In FIG. 1 a mask frame is shown generally at 10. The mask is designed to be worn on a patient's face and is secured by means of straps (not shown) received by attachment points 18.

A conduit end assembly is shown generally at 20, including an elbow part 26 having at one end thereof a combined vent/connector piece 28. The elbow and vent/connector piece together form a housing for an anti-asphyxia valve or other internal components (not shown). At the other end of the elbow is a detachable swivel tube 29 for connection to a gas delivery conduit 71 connected to a gas flow generator 70 structured to supply pressurized gas (see FIG. 1).

The mask 10 includes a circular aperture 12 sized to receive a mating portion 22 of the vent/connector piece 28. The mating portion 22 has an annular groove 23 formed therein that receives a locking means 30 in the form of a C-shaped clip attached after mating to the mask. The clip 30 has an outside diameter greater than the width of the aperture 12 and an inner diameter adapted to ensure a snug fit within the annular groove 23. The clip 30 is resilient and can expand sufficiently to allow the clip to be fitted into and removed from the groove 23. As shown in FIG. 1, the clip 30 is located onto the mating portion 22 or, the inside of the mask 10. In this position, the clip 30 is inaccessible while the mask is being worn by a patient. Once the mating portion 22 of the vent/connector piece 28 has been inserted through the aperture 12 and the locking clip placed in the annular groove, the conduit end assembly 20 and the mask 10 cannot be separated without first removing the mask from the patient.

Figure 2:
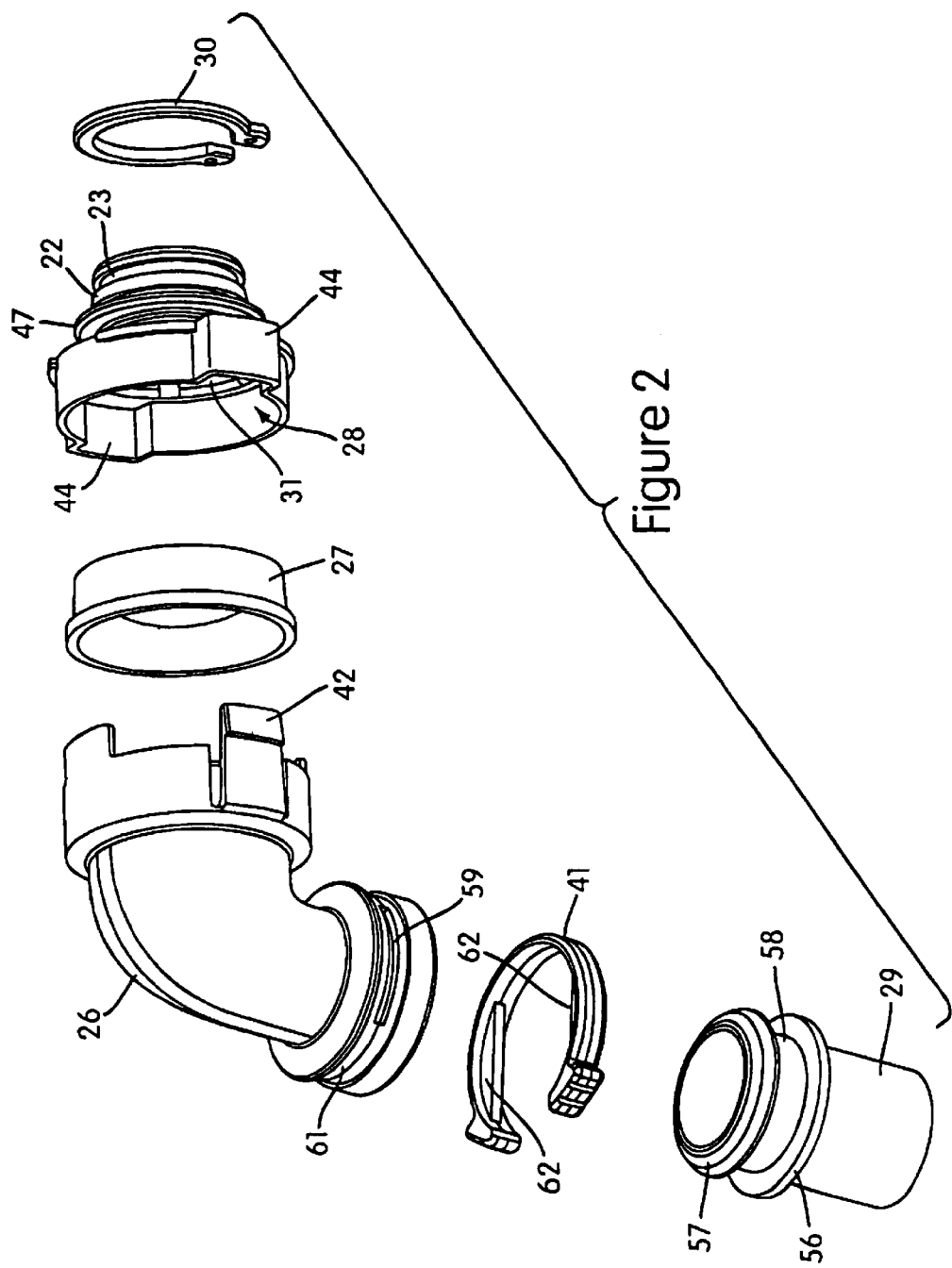
FIG. 2 is an exploded view of the anti-asphyxia valve and conduit connection assembly.

An exploded view of the anti-asphyxia valve and conduit connector assembly is shown in FIG. 2.

The end of the elbow 26 adjacent to the mask 10 is fitted with an anti-asphyxia valve arrangement the provides an air passage to the patient in the event of failure of the gas flow generator 70, including a valve membrane 27 fitted into the end of elbow 26 and vents 31 in the vent/connector piece 28. During proper operation of the gas flow generator 70, the valve membrane remains in the orientation shown in FIG. 2, closing off the vents 31. In the event of a drop in pressure below a predetermined level, the valve membrane 27 flips to a reverse orientation, opening the vents 31. The construction and operation of the anti-asphyxia valve is described in more detail in the Applicant's Australian Patent Application No. 65527/99, the contents of which are incorporated herein by reference.

Resilient detents 42 on the elbow 26 pass through and engage behind slot-forming formations 44 in the vent/connector piece 28 to provide releasable engagement of the two parts.

The vent/connector piece has a color 47 that abuts a corresponding surface of the mask 10 to limit the distance that the vent/connector piece can be inserted into the mask aperture 12 (FIG. 1). The corresponding surface is an annulus 50 having a protruding rim 51 the outer circumference of which preferably engages the inner surface of the detents 42 on insertion of the mating portion 22 into the aperture 12. This engagement prevents the detents from being pushed radially inwards sufficiently for the detents to disengage from behind the slot-forming formations 44, thus preventing the elbow 26 and vent/connector piece 28 from separating whilst still attached to the mask frame 11, for example during patient treatment. The result of this is that the anti-asphyxia valve arrangement cannot be disassembled without first removing the elbow and vent/connector piece assembly from the mask. However, once disconnected from the mask, the assembly may be readily separated for cleaning and then reassembled.

The other, distal end of elbow 26 has an enlarged diameter portion which receives the swivel tube 29, onto which a flexible gas delivery conduit 71 may be fitted. The swivel tube 29 has a pair of flanges 56 and 57 defining an annular grove 58 therebetween. The end of swivel tube 29 is inserted into the elbow 26 until the end flange 57 abuts an inner surface (not shown) within elbow 26. In this position the annular groove 58 is at least partially aligned with an annular groove 61 in the exterior of the elbow, which receives a swivel clip 41.

The swivel clip 41 has an inner diameter only slightly greater than the diameter of the groove 61, to ensure a snug fit within the groove. The clip 41 is resilient to permit sufficient expansion for attachment and removal of the clip from the groove. The groove 61 has slots 59 which receive lugs 62 on the clip. These lugs rotatably engage in the groove 58 between flanges 56 and 57 of the swivel tube. The swivel tube arrangement thus acts as a rotatable coupling between the conduit and the elbow whilst allowing quick attachment and removal of the gas conduit from the elbow regardless of whether the assembly is attached to the mask at the time.

Figure 3:
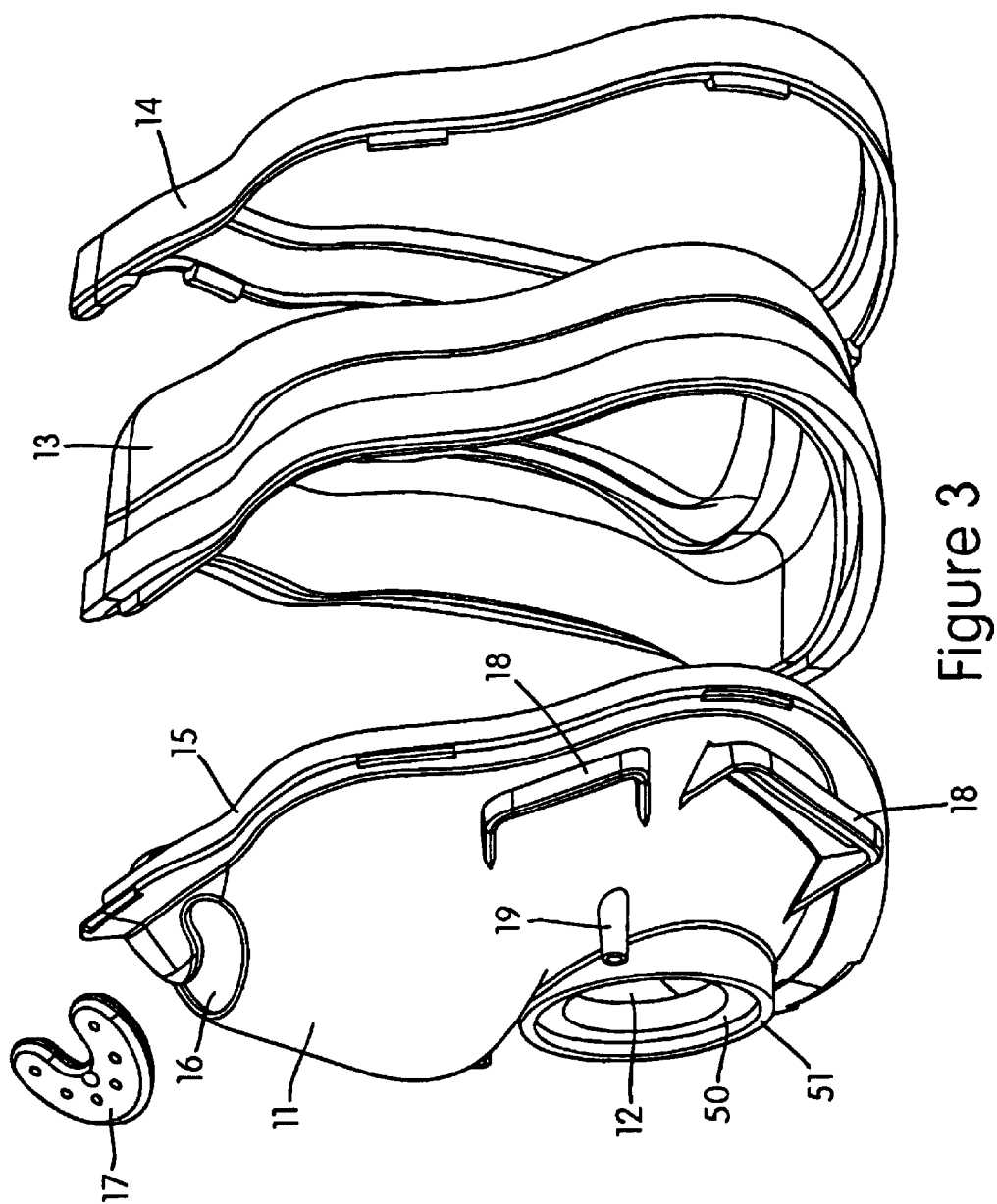
FIG. 3 is an exploded view of the mask assembly.

As shown in FIG. 3, the mask includes a mask fame 11, cushion 13 and cushion clip 14. The cushion is received on a rib 15 extending around He periphery of the mask frame 11. The cushion is held to the rib by the cushion clip 14. The mask frame includes attachment points 18 that receive straps (not shown) for attaching the mask to the patient all aperture 16 for receiving an air vent 17, and measurement ports 19.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

What is claimed is:

1. A patient gas delivery apparatus including:
   a mask structured to communicate with a patient's airway;
   a gas flow generator structured to supply pressurized gas;
   a gas delivery conduit having first and second opposing ends, the first opposing end being connected to the gas flow generator; and
   a connecting assembly including an anti-asphyxia valve member and being connected in series between the conduit and the mask, the connecting assembly having a distal end and a proximal end, the distal end being configured and positioned to connect to the second opposing end of the conduit and the end being configured and positioned to connect to the mask,
   wherein the mask and the conduit are not adapted for direct interconnection without the connecting assembly, and
   wherein the connecting assembly includes a housing having at least two parts connected by an interengagement connector.

2. A patient gas delivery apparatus according to claim 1, wherein a first of the parts includes a rotatable coupling providing the distal end to connect to the second opposing end of the conduit.

3. A patient gas delivery apparatus according to claim 2, wherein a second of the parts includes a mating portion providing the proximal end to connect to the mask.

4. A patient gas delivery apparatus according to claim 3, wherein the mating portion is inserted into an aperture provided in the mask and a lock is attached to the mating portion from an inner side of the mask so as to prevent withdrawal of the mating portion from the aperture.

5. A patient gas delivery apparatus according to claim 2, wherein the housing has at least one vent that is closed by the valve member during normal operation of the apparatus, and opened when pressure falls below a predetermined pressure.

6. A patient gas delivery apparatus according to claim 1, wherein the mask includes an aperture for receiving pressurized air, the connecting assembly including the anti-asphyxia valve member being positioned upstream of the aperture.

7. A patient gas delivery apparatus according to claim 1, further comprising a cushion, the cushion structured to fit over the mask.

8. A patient gas delivery apparatus according to claim 1, wherein the connecting assembly is an elbow joint.

9. A patient gas delivery apparatus according to claim 1, further comprising a cushion, the cushion being removable from the mask independent of the connecting assembly and anti-asphyxia valve thereof.

10. A patient gas delivery apparatus according to claim 1, wherein the anti-asphyxia valve is positioned outside of the mask.

11. A patient gas delivery apparatus apparatus according to claim 1, wherein the proximal end of the connecting assembly defines a receiving space for the valve member and at least one vent aperture positioned radially outward from an outer surface of the valve member.

12. A patient gas delivery apparatus according to claim 11, wherein the at least one vent aperture includes two diametrically opposed vent apertures provided to a detachable vent/connector piece configured to connect to the mask.

13. A patient gas delivery apparatus according to claim 1, wherein the valve member is positioned within a housing including at least one detachable part allowing for the removal of the valve member.

14. A patient gas delivery apparatus including:
a mask having an aperture in communication with a patient's airway;
a gas flow generator structured to supply pressurized gas;
a gas delivery conduit having first and second opposing ends, the first opposing end being connected to the gas flow generator;
a connecting assembly connected in series between the conduit and the mask, the connecting assembly including an elbow portion having a rotatable coupling at a distal end and a mating portion at a proximal end, the rotatable coupling being configured and positioned to connect to the second opposing end of the conduit and the mating portion being configured and positioned to be inserted through the aperture of the mask, the mating portion including a vent connector piece that defines at least one vent aperture and being detachably connected to the elbow portion; and
an anti-asphyxia valve member positioned between the mating portion and the elbow portion,
wherein the mask and the conduit are not adapted for direct interconnection without the connecting assembly.

15. A patient gas delivery apparatus to claim 14, wherein the mask includes an aperture for receiving pressurized air, the connecting assembly including the anti-asphyxia valve member being positioned upstream of the aperture.

16. A patient gas delivery apparatus according to claim 14, further comprising a cushion, the cushion structured to fit over the mask.

17. A patient gas delivery apparatus according to claim 14, further comprising a cushion, the cushion being removable from the mask independent of the connecting assembly and anti-asphyxia valve thereof.

18. A patient gas delivery apparatus according to claim 14, wherein the anti-asphyxia valve is positioned outside of the mask.

19. A patient gas delivery apparatus according to claim 14, wherein the valve member is generally annular and the at least one vent aperture is positioned radially outward from an outer surface of the valve member.

20. A patient gas delivery apparatus according to claim 19, wherein the at least one vent aperture includes diametrically opposed vent apertures.

21. A patient gas delivery apparatus including:
a mask structured to communicate with a patient's airway;
a gas flow generator structured to supply pressurized gas;
a gas delivery conduit having first and second opposing ends, the first opposing end being connected to the gas flow generator; and
a connecting assembly including an anti-asphyxia valve member and being connected in series between the conduit and the mask, the connecting assembly having a distal end and a proximal end, the distal end being configured and positioned to connect to the second opposing end of the condit and the proximal end including a mating portion configured and positioned to connect to the mask,
wherein the valve member is supported within the proximal end adjacent to the mating portion such that the valve member and the mating portion are coaxial with one another, and
wherein the mask and the conduit are not adapted for direct interconnection without the connecting assembly.

22. A patient gas delivery apparatus according to claim 21, wherein the proximal end of the connecting assembly includes a housing having at least two parts connected by an interengagement connector to allow removal of the valve member.

23. A patient gas delivery apparatus according to claim 21, wherein the valve member is generally annualar.

24. A patient gas delivery apparatus according to claim 23, wherein the proximal end of the connecting assembly includes at least one vent aperture positioned radially outward of an outer surface of the valve member.

25. A patient gas delivery apparatus according to claim 24, wherein the at least one aperture includes diametrically opposed vent apertures.

26. A patient gas delivery apparatus including:
a mask structured to communicate with a patient's airway, the mask having a mask frame;
a gas flow generator structured to supply pressurized gas;
a gas delivery conduit having first and second opposing ends, the first opposing end being connected to the gas flow generator; and
a connecting assembly including
(i) an elbow having a first end that connects to the second opposing end of the conduit and a second end including a first engaging portion,
(ii) a vent connector piece having a first end swivelably connected to the mask frame, the first end including a clip retaining portion, the vent connector piece having a second end including a second engaging portion, the second engaging portion adapted to engage with the first engaging portion of the elbow to provide releasable engagement of the vent conncetor piece and the elbow, and
(iii) a valve adapted to be mounted within the vent connector piece, the valve being movable between a normally open position and a closed position upon application of pressure.

27. A patient gas delivery apparatus according to claim 26, wherein the vent connector piece has at least one vent that is closed by the valve during mormal operation of the apparatus and opened when pressure falls below a predetermined pressure.

28. A patient gas delivery apparatus according to claim 26, wherein the clip retaining portion is adapted to be inserted into an aperture of the mask frame and a clip attached to the clip retaining portion so as to prevent withdrawal of the clip retaining portion from the aperture.

29. A patient gas delivery apparatus according to claim 26, wherein one of the first and second engaging portion includes a detent portion and the other of the first and second engaging portions a retaining portion configured to releasably engage with the detent portion.

30. A patient gas delivery apparatus according to claim 26, wherein the valve is generally annular.

31. A patient gas delivery apparatus according to claim 30, wherein the vent connector piece includes at least one vent aperture radially outward of an outer surface of the valve.

32. A patient gas delivery apparatus according to claim 31, wherein the at least one vent aperture includes diametrically opposed vent apertures.

33. A patient gas delivery apparatus according to claim 26, wherein the mask and the conduit are not adapted for direct interconnection without the connecting assembly.

* * * * *